United States Patent
Ooi et al.

(10) Patent No.: US 11,623,040 B2
(45) Date of Patent: Apr. 11, 2023

(54) SENSING CATHETERS

(71) Applicant: Becton, Dickinson and Company, Franklin Lakes, NJ (US)

(72) Inventors: Chun Keat Ooi, Castletroy (IE); Jithendra Kumar, Woodlands (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 48 days.

(21) Appl. No.: 16/912,421

(22) Filed: Jun. 25, 2020

(65) Prior Publication Data

US 2021/0001042 A1 Jan. 7, 2021

Related U.S. Application Data

(60) Provisional application No. 62/870,253, filed on Jul. 3, 2019.

(51) Int. Cl.
| | |
|---|---|
| *A61M 5/168* | (2006.01) |
| *A61M 25/06* | (2006.01) |
| *A61M 5/158* | (2006.01) |
| *A61M 39/10* | (2006.01) |

(52) U.S. Cl.
CPC ........ *A61M 5/16836* (2013.01); *A61M 5/158* (2013.01); *A61M 25/065* (2013.01); *A61M 39/10* (2013.01); *A61M 2005/1588* (2013.01); *A61M 2039/1077* (2013.01); *A61M 2205/587* (2013.01); *A61M 2230/20* (2013.01)

(58) Field of Classification Search
CPC .......... A61M 5/16836; A61M 2230/20; A61M 2005/1588; A61M 2205/15; A61M 5/158; A61M 25/0082; A61M 2025/0166; A61B 5/4848; A61B 5/150992; A61B 5/02042; A61B 5/150748; A61B 5/1535; A61B 5/0538; A61B 5/02028; A61B 5/4839

See application file for complete search history.

(56) References Cited

U.S. PATENT DOCUMENTS

| 8,914,102 B1 | 12/2014 | Rey et al. | |
|---|---|---|---|
| 2008/0172013 A1* | 7/2008 | Kucklick | A61B 5/14539 604/288.03 |

(Continued)

FOREIGN PATENT DOCUMENTS

| WO | 2009/019707 | 2/2009 |
|---|---|---|
| WO | 2017/221223 | 12/2017 |

(Continued)

*Primary Examiner* — Theodore J Stigell
*Assistant Examiner* — Rachel T. Smith
(74) *Attorney, Agent, or Firm* — Kirton McConkie; Whitney Blair; Kevin Stinger (57) ABSTRACT

A catheter system may include a catheter lumen, first and second electrodes, and a sensor in communication with the first and second electrodes. The sensor may be configured to detect at least one of: a bulk volume of blood within a blood vessel and extravasation of a drug from the blood vessel into soft tissue adjacent the blood vessel. Other catheter systems may include a catheter lumen and a sensing chip coupled to the catheter lumen. The sensing chip may be configured to detect at least one of: a bulk volume of blood within a blood vessel and extravasation of a drug from the blood vessel into soft tissue adjacent the blood vessel.

4 Claims, 8 Drawing Sheets

(56) References Cited

U.S. PATENT DOCUMENTS

| | | | |
|---|---|---|---|
| 2013/0338480 A1* | 12/2013 | Hann | A61M 5/158 |
| | | | 600/409 |
| 2014/0296823 A1 | 10/2014 | Ward et al. | |
| 2014/0364715 A1 | 12/2014 | Hauck | |
| 2017/0049359 A1 | 2/2017 | Arevalos et al. | |
| 2017/0259034 A1* | 9/2017 | Leeflang | A61M 25/0053 |
| 2017/0354379 A1* | 12/2017 | Goyal | A61B 5/6848 |

FOREIGN PATENT DOCUMENTS

| | | |
|---|---|---|
| WO | 2018/221223 | 12/2017 |
| WO | 2018/219842 | 12/2018 |
| WO | 2019/010330 | 1/2019 |

\* cited by examiner

SENSING CATHETERS

RELATED APPLICATIONS

This application claims priority to United States Provisional Patent Application No. 62/870,253, filed Jul. 3, 2019 and entitled SENSING CATHETERS which is incorporated herein in its entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral intravenous catheter ("PIVC"). As its name implies, the over-the-needle PIVC may be mounted over an introducer needle having a sharp distal tip. The PIVC and the introducer needle may be assembled so that the distal tip of the introducer needle extends beyond the distal tip of the PIVC with the bevel of the needle facing away from skin of the patient. The PIVC and the introducer needle are generally inserted at a shallow angle through the skin and into a blood vessel of the patient, such as an artery, a vein, or any other vasculature of the patient.

In order to verify proper placement of the introducer needle and/or the PIVC within a blood vessel, a clinician will typically watch for blood "flashback" to occur within the PIVC. Blood flashback occurs when blood travels proximally between an outer surface of the introducer needle and an inner surface of the PIVC, which may be transparent. Thus, the clinician may visualize the blood and confirm placement of the introducer needle within the vasculature. Once placement of the needle has been confirmed, the clinician may temporarily occlude flow in the vein and remove the introducer needle, leaving the PIVC in place for future blood withdrawal and/or fluid infusion.

However, the blood flashback method may also result in false positives due to capillary blood within soft tissues surrounding the blood vessel. This capillary blood may provide a false signal to the clinician before the introducer needle and/or the PIVC have been properly placed within the blood vessel.

Moreover, once a PIVC has been placed within a blood vessel and a drug is delivered to the blood vessel via the PIVC, extravasation of the drug out of the blood vessel and into soft tissues adjacent the blood vessel may occur. A sensor may be attached to the patient's skin close to the catheter insertion site to monitor the patient for drug extravasation events. However, this method of detection may only work after a significant amount of the drug has leaked out of the catheter/blood vessel and migrates close to the patient's skin. Moreover, a sensor placed on the patient's skin is an additional attachment to the patient (and cost) which has to be removed and re-attached periodically (e.g., when the patient needs to go to the bathroom).

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to vascular access devices and related systems and methods.

In some embodiments, a catheter system may include a catheter, which may include a catheter lumen having a proximal end, a distal end, an inner lumen surface, and an outer lumen surface. The catheter may also include first and second electrodes coupled to the catheter lumen. A drug sensor may also be in electrical communication with the first and second electrodes. The distal end of the catheter lumen may be inserted into a blood vessel of a patient such that: (1) at least a portion of the first and second electrodes are embedded within a soft tissue of the patient adjacent the blood vessel; (2) the first and second electrodes are in electrical communication with each other via the soft tissue of the patient between the first and second electrodes; and (3) the drug sensor detects whether extravasation of a drug has occurred from the blood vessel into the soft tissue of the patient by sensing an impedance associated with the soft tissue of the patient.

In some embodiments, the catheter system may include a first attachment feature configured to electrically couple the drug sensor to the first electrode and a second attachment feature configured to electrically couple the drug sensor to the second electrode.

In some embodiments, the first and second electrodes may include electrically conductive material deposited on the outer lumen surface of the catheter and the first and second electrodes may be spaced apart from each other along the outer lumen surface of the catheter.

In some embodiments, the first electrode may include an electrically conductive material placed within a first channel formed along the catheter lumen, the second electrode may include an electrically conductive material placed within a second channel formed along the catheter lumen, and the first and second electrodes may be spaced apart from each other along the outer lumen surface.

In some embodiments, the first and second channels may include open channels and distal portions of the first and second channels may include electrically insulating covers configured to electrically isolate portions of the first and second electrodes that reside within the blood vessel of the patient when the distal end of the catheter lumen is inserted into the blood vessel of the patient.

In some embodiments, the first and second channels may include closed channels and the first and second channels are at least partially skived to allow the first and second electrodes to be in electrical communication with each other via soft tissue between the first and second electrodes.

In some embodiments, the catheter system may include a third electrode including an electrically conductive material placed within a third channel formed along the catheter lumen and the first, second, and third electrodes may be spaced apart from each other along the outer lumen surface.

In some embodiments, a catheter system may include a catheter including a catheter lumen having a proximal end, a distal end, an inner lumen surface, and an outer lumen surface. The catheter may also include first and second electrodes. A blood sensor may be in communication with the first and second electrodes. The distal end of the catheter lumen may be inserted into a blood vessel of a patient such that: (1) at least a portion of the first and second electrodes are embedded within the blood vessel of the patient; (2) the first and second electrodes are in communication with each other via blood residing within the blood vessel of the patient; and (3) the blood sensor detects insertion of the distal end of the catheter lumen into the blood vessel of the patient by sensing at least one characteristic associated with the blood residing within the blood vessel of the patient.

In some embodiments, the at least one characteristic associated with the blood residing within the blood vessel of the patient includes at least one of: an impedance, a capacitance, a pressure, and an electromagnetic signal.

In some embodiments, the catheter system may include a first attachment feature configured to electrically couple the blood sensor to the first electrode and a second attachment feature configured to electrically couple the blood sensor to the second electrode.

In some embodiments, the first and second electrodes include an electrically conductive material deposited on the outer lumen surface, at least portions of the first and second electrodes are located proximate the distal end of the catheter lumen, and the first and second electrodes are spaced apart from each other on the outer lumen surface of the catheter lumen.

In some embodiments, the electrically conductive material includes an electrically conductive ink.

In some embodiments, the catheter lumen is made of an electrically conductive plastic, the catheter lumen includes the first electrode, the catheter system further includes an introducer needle, and the introducer needle includes the second electrode.

In some embodiments, the blood sensor is configured to detect when the distal end of the catheter lumen is inserted into the blood vessel of the patient by sensing an electrical characteristic associated with the blood residing within the blood vessel of the patient between the catheter lumen and the introducer needle.

In some embodiments, the inner lumen surface of the catheter lumen further includes an electrically insulating layer and the blood sensor is configured to detect when the distal end of the catheter lumen is inserted into the blood vessel of the patient by sensing an electrical characteristic associated with the blood residing within the blood vessel of the patient between the distal end of the catheter lumen and a distal portion of the introducer needle.

In some embodiments, a catheter system may include a catheter including a catheter lumen having a proximal end, a distal end, an inner lumen surface, and an outer lumen surface. The catheter may also include a drug sensing chip coupled to the catheter lumen. When the distal end of the catheter lumen is inserted into a blood vessel of a patient: (1) at least a portion of the drug sensing chip may be embedded within a soft tissue of the patient adjacent the blood vessel; and (2) the drug sensing chip can detect whether extravasation of a drug has occurred from the blood vessel into the soft tissue of the patient.

In some embodiments, the drug sensing chip is configured to detect extravasation of the drug from the blood vessel into the soft tissue of the patient by sensing an impedance associated with the soft tissue of the patient.

In some embodiments, the drug sensing chip is configured to detect extravasation of the drug from the blood vessel into the soft tissue of the patient by sensing at least one of: a pressure associated with the soft tissue of the patient, a capacitance associated with the soft tissue of the patient, and an infrared signal associated with the soft tissue of the patient.

In some embodiments, the drug sensing chip includes an output configured to provide an indication when extravasation of a drug from the blood vessel into the soft tissue of the patient has been detected. In some embodiments, the output includes an LED.

It is to be understood that both the foregoing general description and the following detailed description are exemplary and explanatory and are not restrictive of the embodiments of the present disclosure, as claimed. It should be understood that the various embodiments of the present disclosure are not limited to the arrangements and instrumentality shown in the drawings. It should also be understood that the embodiments of the present disclosure may be combined, or that other embodiments may be utilized and that structural changes, unless so claimed, may be made without departing from the scope of the various embodiments of the present disclosure. The following detailed description is, therefore, not to be taken in a limiting sense.

BRIEF DESCRIPTION OF THE DRAWINGS

Example embodiments will be described and explained with additional specificity and detail through the use of the accompanying drawings in which.

It is to be understood that the Figures are for purposes of illustrating the concepts of the present disclosure and may not be drawn to scale. Furthermore, the Figures illustrate exemplary embodiments and do not represent limitations to the scope of the present disclosure.

DESCRIPTION OF EMBODIMENTS

Exemplary embodiments of the present disclosure will be best understood by reference to the Figures, wherein like parts are designated by like numerals throughout. It will be readily understood that the components of the present disclosure, as generally described and illustrated in the Figures herein, could be arranged and designed in a wide variety of different configurations. Thus, the following more detailed description of the embodiments of the apparatus, systems, and methods, as represented in the Figures, is not intended to limit the scope of the present disclosure, as claimed in this or any other application claiming priority to this application, but is merely representative of exemplary embodiments of the present disclosure.

Figure 1A:
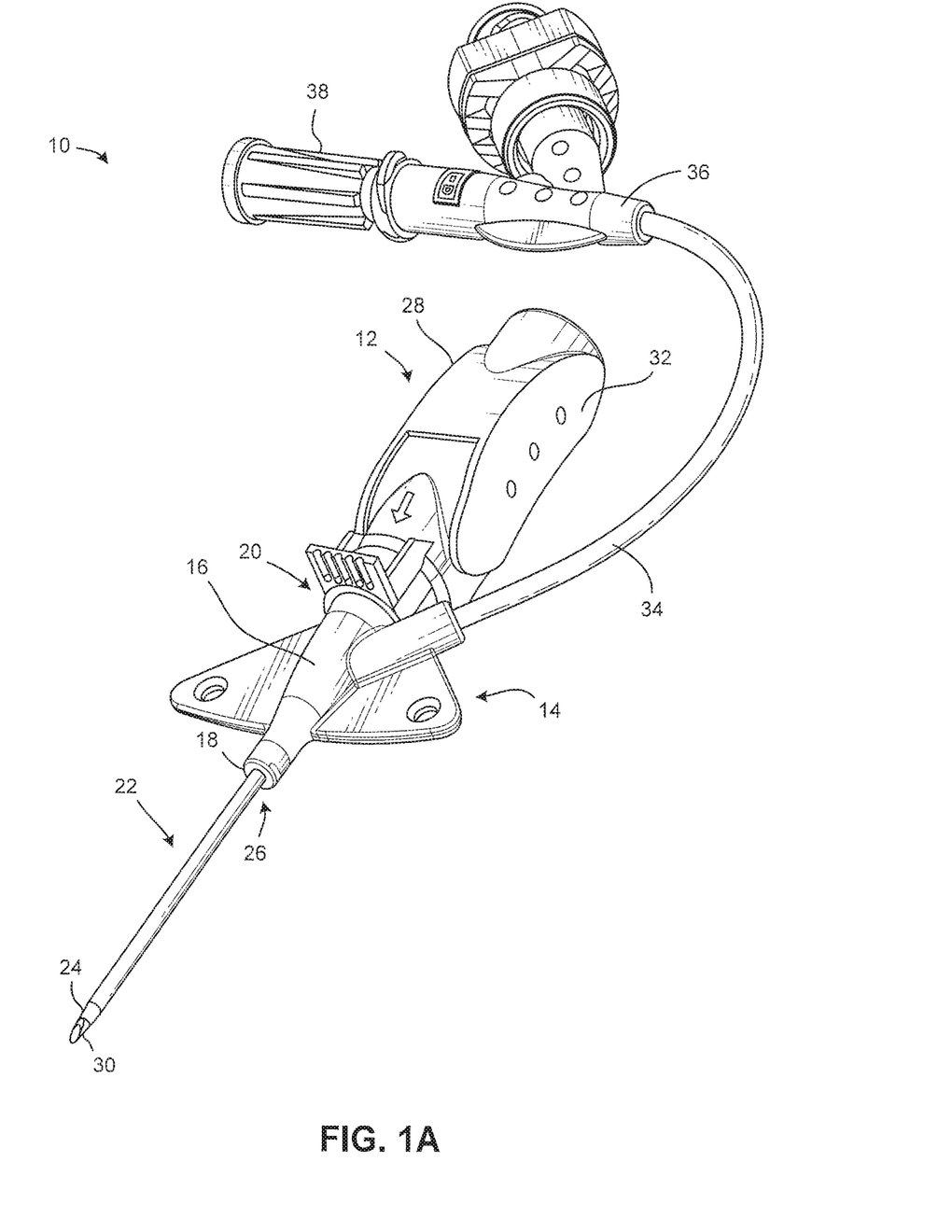
FIG. 1A is an upper perspective view of an example catheter system 10, according to some embodiments.
Figure 1B:
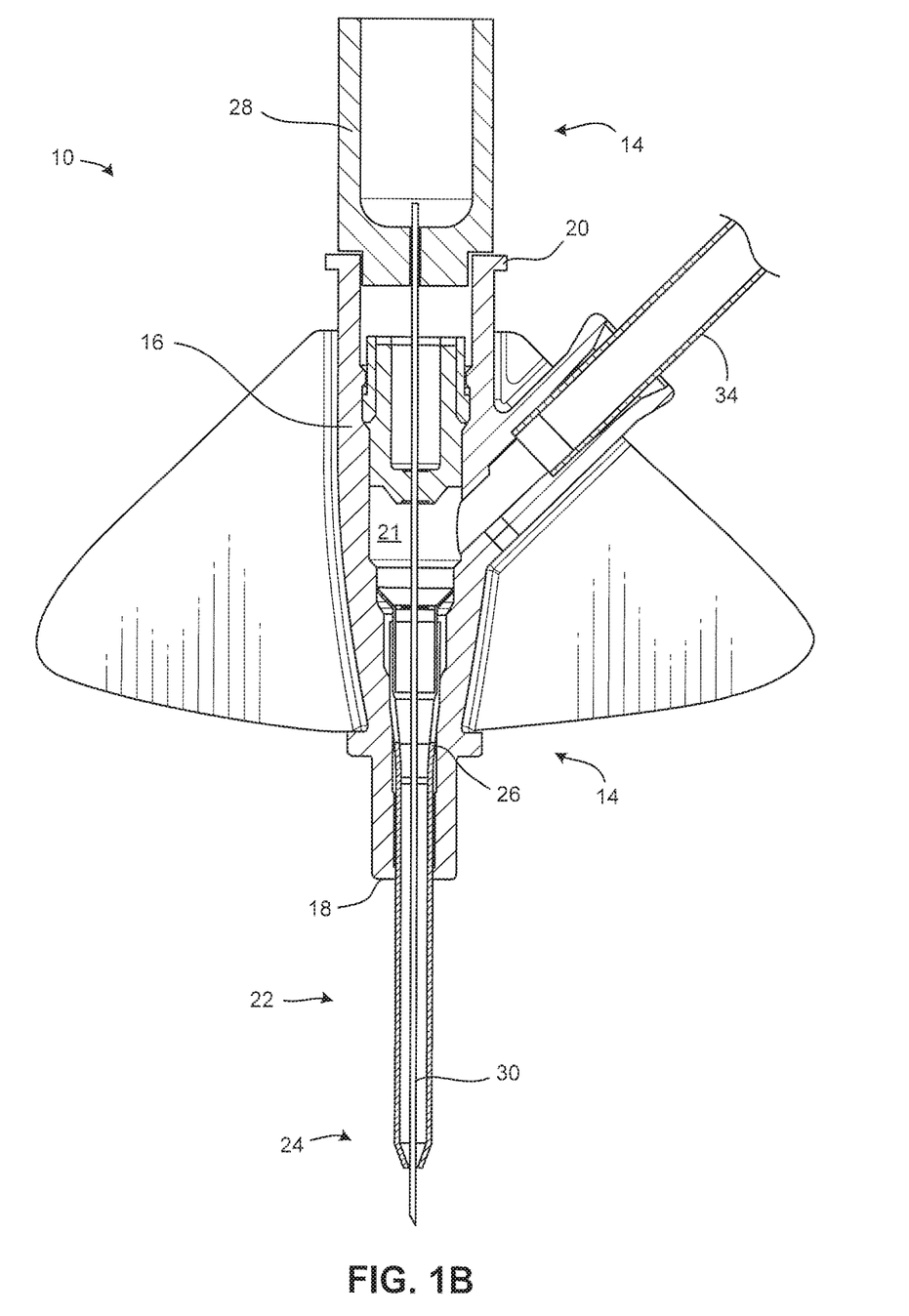
FIG. 1B is a cross-sectional top view of the catheter system 10 of FIG. 1A, according to some embodiments.

Referring to FIGS. 1A and 1B, in some embodiments, a catheter system 10 may include a needle assembly 12 and a catheter assembly 14. FIGS. 1A and 1B illustrate the catheter system 10 in an insertion position, ready for insertion into a vein of a patient (not shown), according to some embodiments. In some embodiments, the catheter assembly 14 may include a catheter adapter 16, which may include a distal end 18, a proximal end 20, and a catheter assembly lumen 21 extending through the distal end 18 and the proximal end 20. In some embodiments, the catheter assembly 14 may include a catheter 22, which may include a distal end 24 and a proximal end 26. In some embodiments, the catheter 22 may include a peripheral intravenous catheter ("PIVC"). In some embodiments, the proximal end 26 of the catheter 22 may be secured within the catheter adapter 16.

In some embodiments, the needle assembly 12 may include a needle hub 28, which may be removably coupled to the catheter adapter 16. In some embodiments, the needle assembly 12 may include an introducer needle 30. In some embodiments, a proximal end of the introducer needle 30 may be secured within the needle hub 28. In some embodiments, the introducer needle 30 may extend through the catheter 22 when the catheter system 10 is in an insertion position ready for insertion into the vein of a patient, as illustrated, for example, in FIGS. 1A and 1B.

In some embodiments, the needle assembly 12 may include a needle grip 32, which a clinician may grip and move proximally to withdraw the introducer needle 30 from the vein once placement of the catheter 22 within the vein is confirmed. In some embodiments, the catheter system 10 may include an extension tube 34. In some embodiments, a distal end of the extension tube 34 may be coupled to the catheter adapter 16 and a proximal end of the extension tube 34 may be coupled to an adapter 36.

In some embodiments, a fluid infusion device (not shown) may be coupled to the adapter 36 to deliver fluid to the patient via the catheter 22 inserted in the vein, once the introducer needle 30 is removed from the catheter system 10. In some embodiments, a blood collection device (not shown) may be coupled to the adapter 36 to withdraw blood from the patient via the catheter 22 inserted in the vein.

In some embodiments, the catheter system 10 may be integrated, having the extension tube 34 integrated within the catheter adapter 16, such as, for example, the BD NEXIVA™ Closed IV Catheter System, the BD NEXIVA™ DIFFUSICS™ Closed IV Catheter System, the BD PEGASUS™ Safety Closed IV Catheter System, or another integrated catheter system. An example of an integrated catheter system 10 is illustrated in FIGS. 1A and 1B. In some embodiments, the catheter system 10 may be non-integrated, without the extension tube 34.

In some embodiments, the catheter system 10 may be vented to observe blood and facilitate proximal flow of blood within the introducer needle 30 and/or the catheter 22. In some embodiments, the catheter system 10 may be vented in any suitable manner. For example, a vent plug 38 may be coupled to the adapter 36 during insertion of the catheter assembly 14 into the patient. In some embodiments, the vent plug 38 may be permeable to air but not to blood. In some embodiments, the catheter 22, the catheter adapter 16, the extension tube 34, the adapter 36, and the vent plug 38 may be in fluid communication. As another example, in some embodiments, the needle hub 28 may include a flash chamber.

Figure 2:
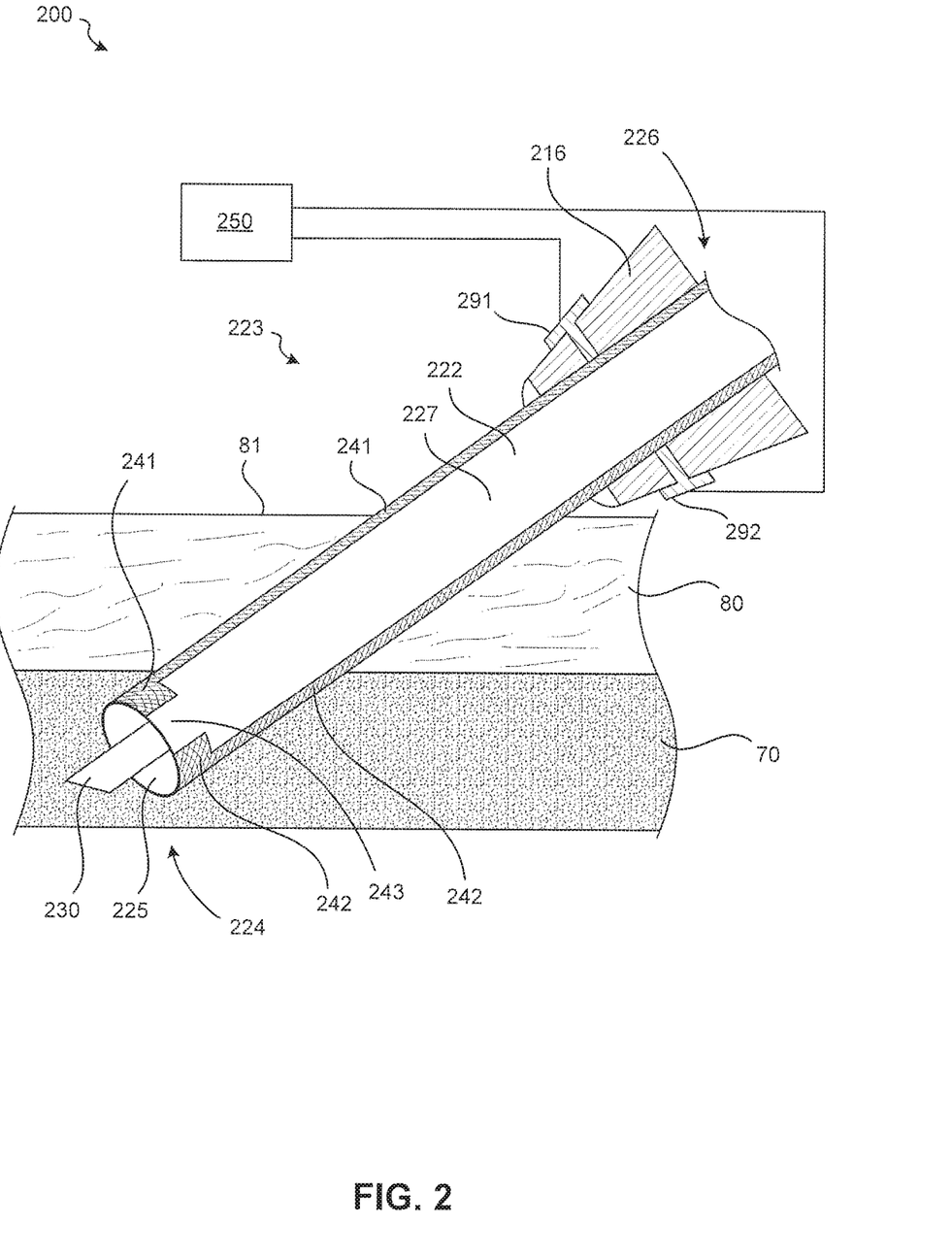
FIG. 2 is a partial cross-sectional side view of an example catheter system 200 inserted into tissue, according to some embodiments.

FIG. 2 illustrates a partial cross-sectional side view of an example catheter system 200 inserted into soft tissue, according to some embodiments. The catheter system 200 may generally include a catheter 223, a catheter adapter 216, an introducer needle 230, and a sensor 250. As shown in FIG. 2, the catheter 223 may be inserted through the skin 81 and into the soft tissue 80, until a distal portion of the catheter 223 enters a blood vessel 70.

The catheter 223 may include a catheter lumen 222 having a proximal end 226, a distal end 224, an inner lumen surface 225, and an outer lumen surface 227. Although not shown in FIG. 2, in some embodiments, the distal end 224 of the catheter 223 may also be tapered, similar to the tapered distal end 24 of the catheter 22 illustrated in FIGS. 1A and 1B.

The catheter system 200 may also include a first electrode 241 and a second electrode 242. In the embodiment shown in FIG. 2, the first and second electrodes 241, 242 may be coupled to the outer lumen surface 227 of the catheter 223, extending along a length of the catheter 223. However, it will also be understood that in other embodiments (not shown), the first and second electrodes 241, 242 may alternatively, or in addition thereto, be coupled to the inner lumen surface 225 of the catheter 223. The first and second electrodes 241, 242 may also be spaced apart from each other along the outer lumen surface 227 and/or along the inner lumen surface 225. In some embodiments, at least a portion of the first electrode 241 and a portion of the second electrode 242 may be located proximate the distal end 224 of the catheter 223. In some embodiments, the portions of the first and second electrodes 241, 242 located proximate the distal end 224 of the catheter 223 may extend toward each other to create an electrode gap 243 proximate the distal end 224 of the catheter 223. In some embodiments, an orientation, direction, or distance of the electrode gap 243 may vary. In some embodiments, the first and second electrodes 241, 242 may include an electrically conductive material deposited on a surface of the catheter 223, such as the outer lumen surface 227 and/or the inner lumen surface 225. In some embodiments, the electrically conductive material may include an electrically conductive ink.

The catheter system 200 may also include a first attachment feature 291 configured to couple the first electrode 241 to the sensor 250, and a second attachment feature 292 configured to couple the second electrode 242 to the sensor 250. The first and second attachment features 291, 292 may be coupled to, and/or integrated with, the catheter adapter 216. However, in other embodiments (not shown), the first and second attachment features 291, 292 may be directly coupled to, and/or integrated with, the catheter 223. In some embodiments, the first and second attachment features 291, 292 may traverse between an outer surface of the catheter adapter 216 and an inner surface of the catheter adapter 216. In some embodiments, the first attachment feature 291 may directly, or indirectly, contact the first electrode 241, and the second attachment feature 292 may directly, or indirectly, contact the second electrode 242. In some embodiments, the first and second attachment features 291, 292 may be configured to electrically couple the first and second electrodes 241, 242 to the sensor 250.

In some embodiments, the sensor 250 may be a blood sensor 250 configured to sense a bulk volume of blood within the blood vessel 70. In this manner, the blood sensor 250 may detect when the distal end 224 of the catheter 223 has been successfully inserted into the blood vessel 70, and an indication of successful insertion may be provided to the clinician via any suitable output device known in the art. For example, a bulk volume of blood within the blood vessel 70 can exhibit different electrical, chemical, and/or physical characteristics in comparison to capillary blood dispersed within the soft tissue 80 adjacent the blood vessel 70. These differences in electrical, chemical, and/or physical characteristics may be utilized to indicate whether or not the catheter 223 has been properly inserted within the blood vessel 70 in order to achieve less false positives indicating a successful insertion, in comparison to utilizing the blood flashback method alone.

In some embodiments, the blood sensor 250 may be in communication with the first and second electrodes 241, 242 such that, when the distal end 224 of the catheter lumen 222 is successfully inserted into the blood vessel 70: (1) at least a portion of the first and second electrodes 241, 242 are embedded within the blood vessel 70; (2) the first and second electrodes 241, 242 are in communication with each other via blood residing within the blood vessel 70; and (3) the blood sensor 250 detects successful insertion of the distal end 224 of the catheter lumen 222 within the blood vessel 70 by sensing at least one characteristic associated with the blood residing within the blood vessel 70.

In some embodiments, the at least one characteristic associated with the blood residing within the blood vessel 70 includes at least one of: an impedance, a capacitance, a conductance, an inductance, an electromagnetic signal, a pressure, and a temperature. In some embodiments, the at least one characteristic may be measured directly, or indirectly. In some embodiments, determination of successful insertion may be based on a threshold value associated with the at least one characteristic, a change detected in the at least one characteristic as the distal end 224 of the catheter lumen 222 is inserted into the blood vessel 70, and/or a relative difference that is detected in the at least one characteristic as the distal end 224 of the catheter lumen 222 is inserted into the blood vessel 70.

Figure 3:
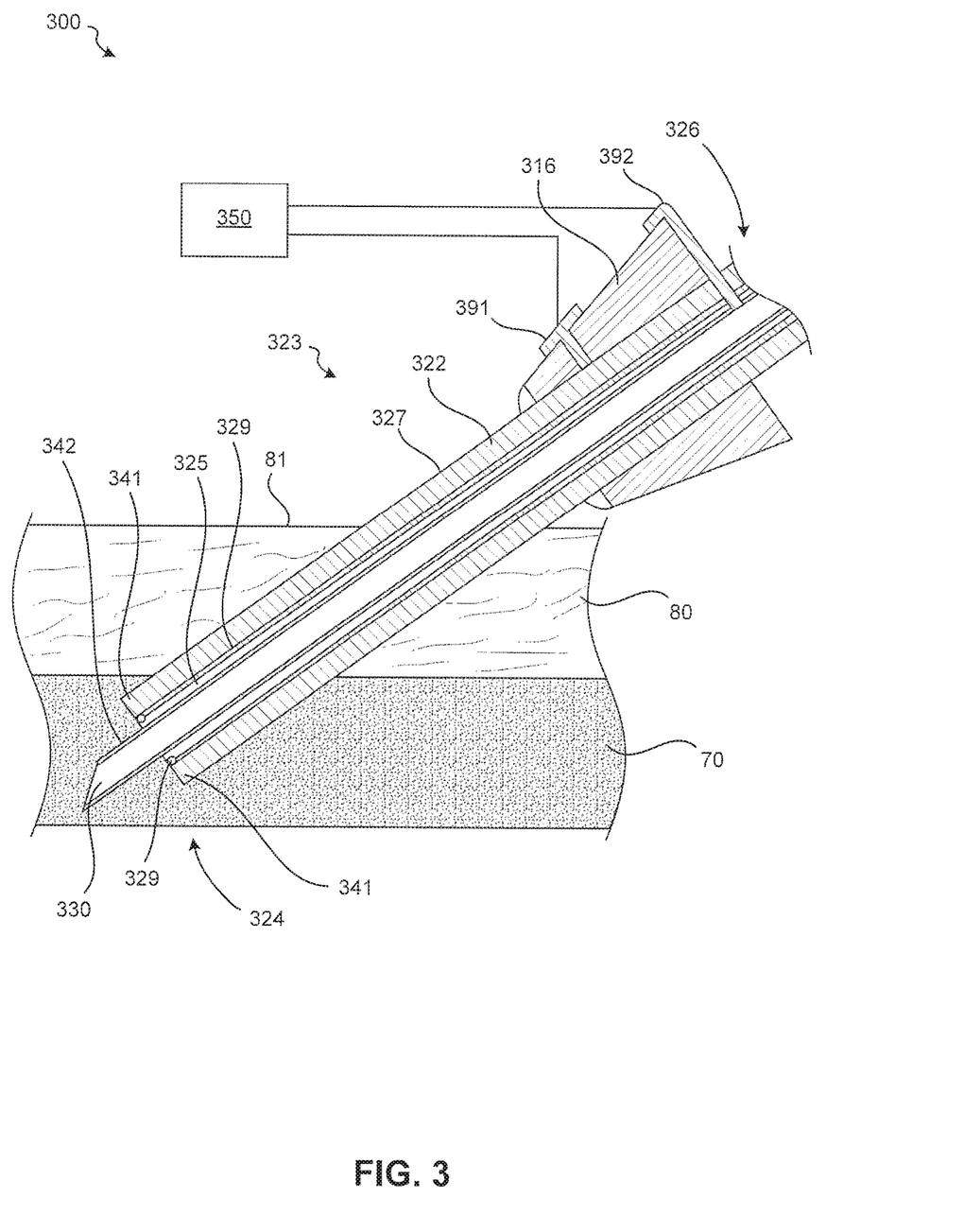
FIG. 3 is a cross-sectional side view of an example catheter system 300 inserted into tissue, according to some embodiments.

FIG. 3 illustrates a cross-sectional side view of an example catheter system 300 inserted into soft tissue 80, according to some embodiments. The catheter system 300 may generally include a catheter 323, a catheter adapter 316, an introducer needle 330, and a sensor 350. As shown in FIG. 3, the catheter 323 may be inserted through the skin 81 and into the soft tissue 80, until a distal portion of the catheter 323 enters the blood vessel 70.

The catheter 323 may include a catheter lumen 322 having a proximal end 326, a distal end 324, an inner lumen surface 325, and an outer lumen surface 327. Although not shown in FIG. 3, in some embodiments, the distal end 324 of the catheter 323 may also be tapered, similar to the tapered distal end 24 of the catheter 22 illustrated in FIGS. 1A and 1B.

The catheter system 300 may also include a first electrode 341 and a second electrode 342. In the embodiment shown in FIG. 3, the catheter lumen 322 may include the first electrode 341, and the introducer needle 330 may include the second electrode 342. For example, in some embodiments, the catheter lumen 322 may be made of an electrically conductive material. In some embodiments, the electrically conductive material of the catheter lumen 322 may include an electrically conductive plastic. In some embodiments, the catheter lumen 322 may also include a radiopaque material. Additionally, in some embodiments, the introducer needle 330 may include an electrically conductive material. In some embodiments, the electrically conductive material of the introducer needle 330 may include an electrically conductive metal. In some embodiments, at least a portion of the first electrode 341 and a portion of the second electrode 342 may be located proximate the distal end 324 of the catheter 323.

In some embodiments, the inner lumen surface 325 of the catheter lumen 322 may include an electrically insulating layer 329 or material. This electrically insulating layer 329 may be configured to electrically insulate the first electrode 341 (e.g., the catheter 323) from the second electrode 342 (e.g., the introducer needle 330). In some embodiments, the electrically insulating layer 329 may be coupled to the inner lumen surface 325 of the catheter lumen 322 via a coating process. In some embodiments, the electrically insulating layer 329 may be integrated with the catheter 323 via a co-extrusion process.

The catheter system 300 may also include a first attachment feature 391 configured to couple the first electrode 341 to the sensor 350, and a second attachment feature 392 configured to couple the second electrode 342 to the sensor 350. The first and second attachment features 391, 392 may be coupled to, and/or integrated with, the catheter adapter 316, and/or a needle assembly/hub (not shown in FIG. 3). However, in other embodiments (not shown), the first and second attachment features 391, 392 may be directly coupled to, and/or integrated with, the catheter 323 and the introducer needle 330. In some embodiments, the first and second attachment features 391, 392 may traverse between an outer surface of the catheter adapter 316 (and/or a needle assembly/hub) and an inner surface of the catheter adapter 316 (and/or a needle assembly/hub). In some embodiments, the first attachment feature 391 may directly, or indirectly, contact the first electrode 341, and the second attachment feature 392 may directly, or indirectly, contact the second electrode 342. In some embodiments, the first and second attachment features 391, 392 may be configured to electrically couple the first and second electrodes 341, 342 to the sensor 350.

In some embodiments, the sensor 350 may be a blood sensor 350 configured to sense a bulk volume of blood within the blood vessel 70. In this manner, the blood sensor 350 may detect when the distal end 324 of the catheter 323 has been successfully inserted into the blood vessel 70, and an indication of successful insertion may be provided to the clinician via any suitable output device known in the art. As previously discussed, a bulk volume of blood within the blood vessel 70 can exhibit different electrical, chemical, and/or physical characteristics in comparison to capillary blood dispersed within the soft tissue 80 adjacent the blood vessel 70. These differences in electrical, chemical, and/or physical characteristics may be utilized to indicate whether or not the catheter 323 has been properly inserted within the blood vessel 70 in order to achieve less false positives of indicating a successful insertion, in comparison to utilizing the blood flashback method alone.

In some embodiments, the blood sensor 350 may be in communication with the first and second electrodes 341, 342 such that, when the distal end 324 of the catheter lumen 322 is successfully inserted into the blood vessel 70: (1) at least a portion of the first and second electrodes 341, 342 are embedded within the blood vessel 70; (2) the first and second electrodes 341, 342 are in communication with each other via blood residing within the blood vessel 70; and (3) the blood sensor 350 detects successful insertion of the distal end 324 of the catheter lumen 322 into the blood vessel 70 by sensing at least one characteristic associated with the blood residing within the blood vessel 70.

In some embodiments, the at least one characteristic associated with the blood residing within the blood vessel 70 includes at least one of: an impedance, a capacitance, a conductance, an inductance, an electromagnetic signal, a pressure, and a temperature. In some embodiments, the at least one characteristic may be measured directly, or indirectly. In some embodiments, determination of successful insertion may be based on a threshold value associated with the at least one characteristic, a change detected in the at least one characteristic as the distal end 324 of the catheter lumen 322 is inserted into the blood vessel 70, and/or a relative difference that is detected in the at least one characteristic as the distal end 324 of the catheter lumen 322 is inserted into the blood vessel 70.

In some embodiments, the blood sensor 350 is configured to detect when the distal end of the catheter lumen 322 is inserted into the blood vessel 70 by sensing an electrical characteristic associated with the blood residing within the blood vessel 70 between the catheter lumen 322 and the introducer needle 330.

In some embodiments, the blood sensor 350 is configured to detect when the distal end 324 of the catheter lumen 322 is inserted into the blood vessel 70 by sensing an electrical characteristic associated with the blood residing within the blood vessel 70 between the distal end 324 of the catheter lumen 322 and a distal portion of the introducer needle 330.

Figure 4:
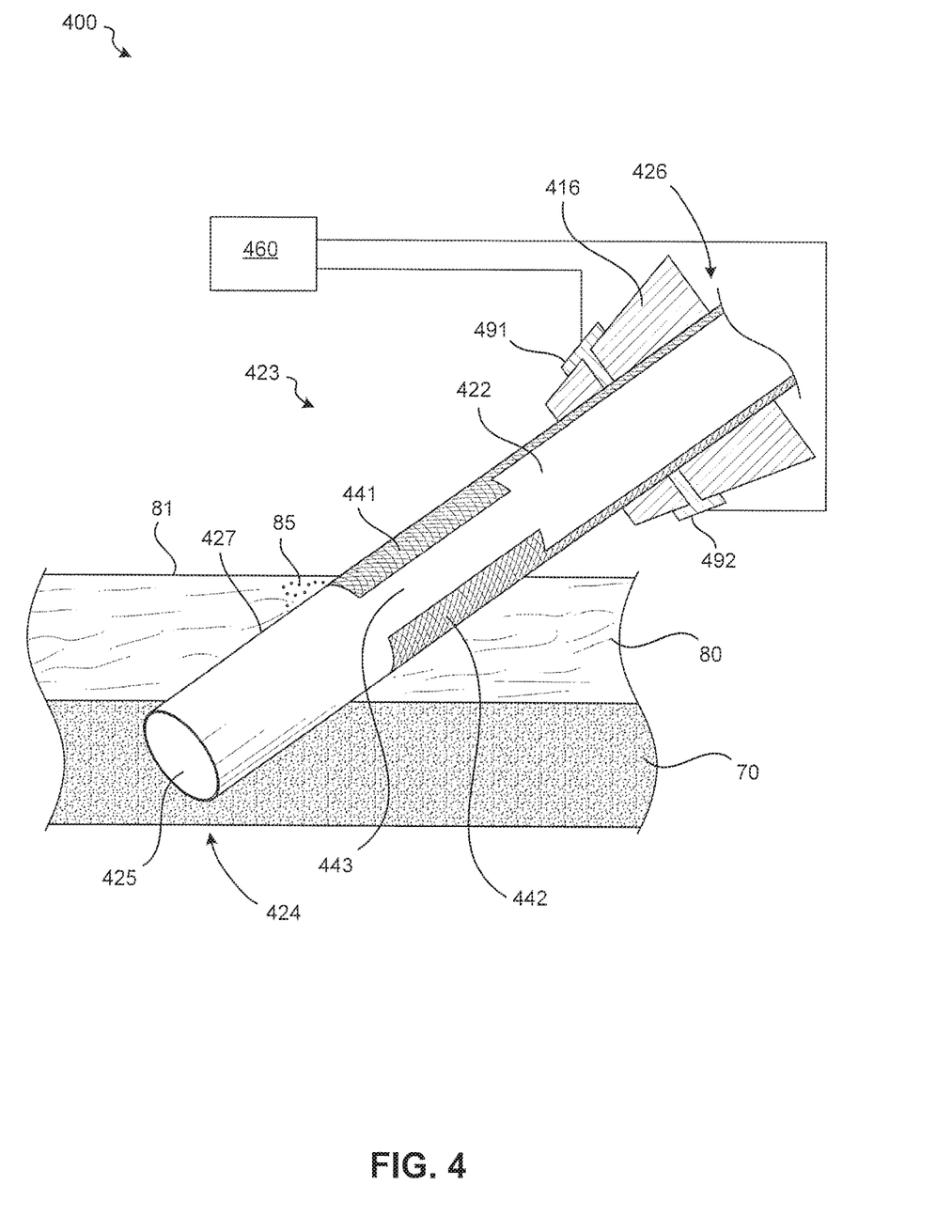
FIG. 4 is a partial cross-sectional side view of an example catheter system 400 inserted into tissue, according to some embodiments.

FIG. 4 illustrates a partial cross-sectional side view of an example catheter system 400 inserted into soft tissue, according to some embodiments. The catheter system 400 may generally include a catheter 423, a catheter adapter 416, and a sensor 460. As shown in FIG. 4, the catheter 423 may be inserted through the skin 81 and into the soft tissue 80 until a distal portion of the catheter 423 enters the blood vessel 70.

The catheter 423 may include a catheter lumen 422 having a proximal end 426, a distal end 424, an inner lumen surface 425, and an outer lumen surface 427. Although not shown in FIG. 4, in some embodiments, the distal end 424 of the catheter 423 may also be tapered, similar to the tapered distal end 24 of the catheter 22 illustrated in FIGS. 1A and 1B.

The catheter system 400 may also include a first electrode 441 and a second electrode 442. In the embodiment shown in FIG. 4, the first and second electrodes 441, 442 may be coupled to the outer lumen surface 427 of the catheter 423, extending along a length of the catheter 423. However, it will also be understood that in other embodiments (not shown), the first and second electrodes 441, 442 may alternatively, or in addition thereto, be coupled to the inner lumen surface 425 of the catheter 423. The first and second electrodes 441, 442 may also be spaced apart from each other along the outer lumen surface 427 and/or along the inner lumen surface 425 at one or more distances.

In some embodiments, at least a portion of the first electrode 441 and a portion of the second electrode 442 may be embedded within the soft tissue 80 adjacent the blood vessel 70 when the distal end 424 of the catheter lumen 422 is inserted into the blood vessel 70. In some embodiments, portions of the first and second electrodes 441, 442 may extend toward each other to create an electrode gap 443 located intermediate the proximal and distal ends 426, 424 of the catheter 423. In some embodiments, an orientation, direction, or distance of the electrode gap 443 may vary. In some embodiments, the first and second electrodes 441, 442 may include an electrically conductive material deposited on a surface of the catheter 423, such as the outer lumen surface 427 and/or the inner lumen surface 425. In some embodiments, the electrically conductive material may include an electrically conductive ink.

The catheter system 400 may also include a first attachment feature 491 configured to couple the first electrode 441 to the sensor 460, and a second attachment feature 492 configured to couple the second electrode 442 to the sensor 460. The first and second attachment features 491, 492 may be coupled to, and/or integrated with, the catheter adapter 416. However, in other embodiments (not shown), the first and second attachment features 491, 492 may be directly coupled to, and/or integrated with, the catheter 423. In some embodiments, the first and second attachment features 491, 492 may traverse between an outer surface of the catheter adapter 416 and an inner surface of the catheter adapter 416. In some embodiments, the first attachment feature 491 may directly, or indirectly, contact the first electrode 441, and the second attachment feature 492 may directly, or indirectly, contact the second electrode 442. In some embodiments, the first and second attachment features 491, 492 may be configured to electrically couple the first and second electrodes 441, 442 to the sensor 460.

In some embodiments, the sensor 460 may be a drug sensor 460 configured to sense when a drug 85 has leaked out of the blood vessel 70 and into the soft tissue 80 adjacent the blood vessel 70 via an extravasation process. In this manner, the drug sensor 460 may detect when extravasation of the drug 85 has occurred and an indication of drug extravasation may be provided to the clinician via any suitable output device known in the art. For example, soft tissue containing an extravasated drug can exhibit different electrical, chemical, and/or physical characteristics in comparison to soft tissue that does not contain an extravasated drug. These differences in electrical, chemical, and/or physical characteristics may be utilized to indicate whether or not the soft tissue contains an extravasated drug in order to alert the clinician to a possible dangerous situation.

In some embodiments, the drug sensor 460 may be in communication with the first and second electrodes 441, 442 coupled to the catheter lumen 422 such that, when the distal end 424 of the catheter lumen 422 is successfully inserted into the blood vessel 70: (1) at least a portion of the first and second electrodes 441, 442 are embedded within the soft tissue 80 adjacent the blood vessel 70; (2) the first and second electrodes 441, 442 are in communication with each other through the soft tissue 80 between the first and second electrodes 441, 442; and (3) the drug sensor 460 detects whether extravasation of the drug 85 has occurred from the blood vessel 70 into the soft tissue 80 by sensing a characteristic associated with the soft tissue 80.

In some embodiments, the at least one characteristic associated with the soft tissue 80 containing the extravasated drug 85 includes at least one of: an impedance, a capacitance, a conductance, an inductance, an electromagnetic signal, a pressure, and a temperature. In some embodiments, the at least one characteristic may be measured directly, or indirectly. In some embodiments, determination of drug 85 extravasation may be based on a threshold value associated with the at least one characteristic, a change detected in the at least one characteristic as the soft tissue 80 becomes infused with the drug 85, and/or a relative difference that is detected in the at least one characteristic as the soft tissue 80 becomes infused with the drug 85.

Figure 5:
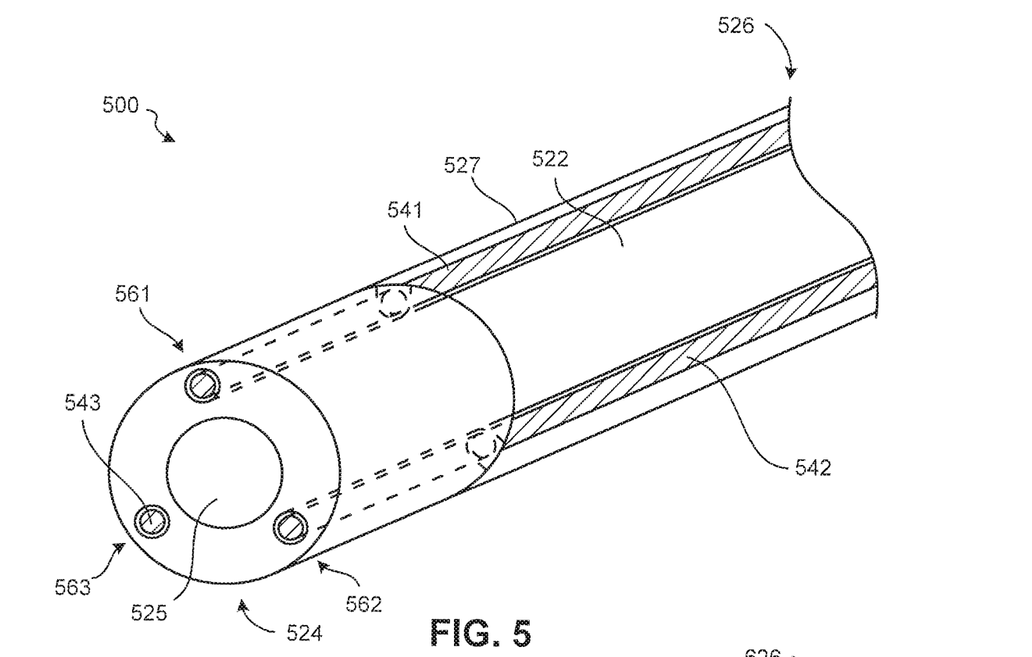
FIG. 5 is a perspective side view of an example catheter 500, according to some embodiments.

FIG. 5 illustrates a perspective side view of an example catheter 500 which may be utilized to detect drug extravasation, according to some embodiments. The catheter 500 may include a catheter lumen 522 having a proximal end 526, a distal end 524, an inner lumen surface 525, and an outer lumen surface 527. Although not shown in FIG. 5, in some embodiments, the distal end 524 of the catheter 500 may also be tapered, similar to the tapered distal end 24 of the catheter 22 illustrated in FIGS. 1A and 1B.

The catheter 500 may include a first electrode 541, a second electrode 542, and a third electrode 543. However, in other embodiments (not shown), the catheter 500 may only include two electrodes. In still other embodiments (not shown), the catheter 500 may include more than three electrodes.

In some embodiments, the first, second, and third electrodes 541, 542, 543 may include an electrically conductive material. In some embodiments, the electrically conductive material may include an electrically conductive metal. The first, second, and third electrodes 541, 542, 543 may also be spaced apart from each other along the catheter 500 and/or the outer lumen surface 527.

In the embodiment shown in FIG. 5, the first, second, and third electrodes 541, 542, 543 may each be coupled to the catheter within a first channel 561, a second channel 562, and a third channel 563, respectively. The first, second, and third channels 561, 562, 563 may also extend along a length of the catheter 500. The first, second, and third channels 561, 562, 563 may include closed channels formed within the body of the catheter lumen 522 in order to electrically insulate the first, second, and third electrodes 541, 542, 543 from each other.

The first, second, and third electrodes/channels 541, 542, 543, 561, 562, 563 may be formed by co-extruding the first, second, and third electrodes 541, 542, 543 with the catheter 500. In some embodiments, the first, second, and third channels 561, 562, 563 may then undergo a skiving process to expose portions of the first, second, and third electrodes 541, 542, 543. This skiving process may include removing catheter material that is above the first, second, and third electrodes 541, 542, 543 to expose them and allow the first, second, and third electrodes 541, 542, 543 to be in electrical communication with each other via soft tissue 80 between the first, second, and third electrodes 541, 542, 543. In some embodiments, a distal portion of the catheter 500 may not be skived, in order to keep the first, second, and third electrodes 541, 542, 543 electrically isolated from each other at the distal portion of the catheter 500. In this manner, the first, second, and third electrodes 541, 542, 543 at the distal portion of the catheter 500 (which enters into a blood vessel) will not sense a drug within the blood vessel and produce a false positive indication for drug extravasation.

Figure 6:
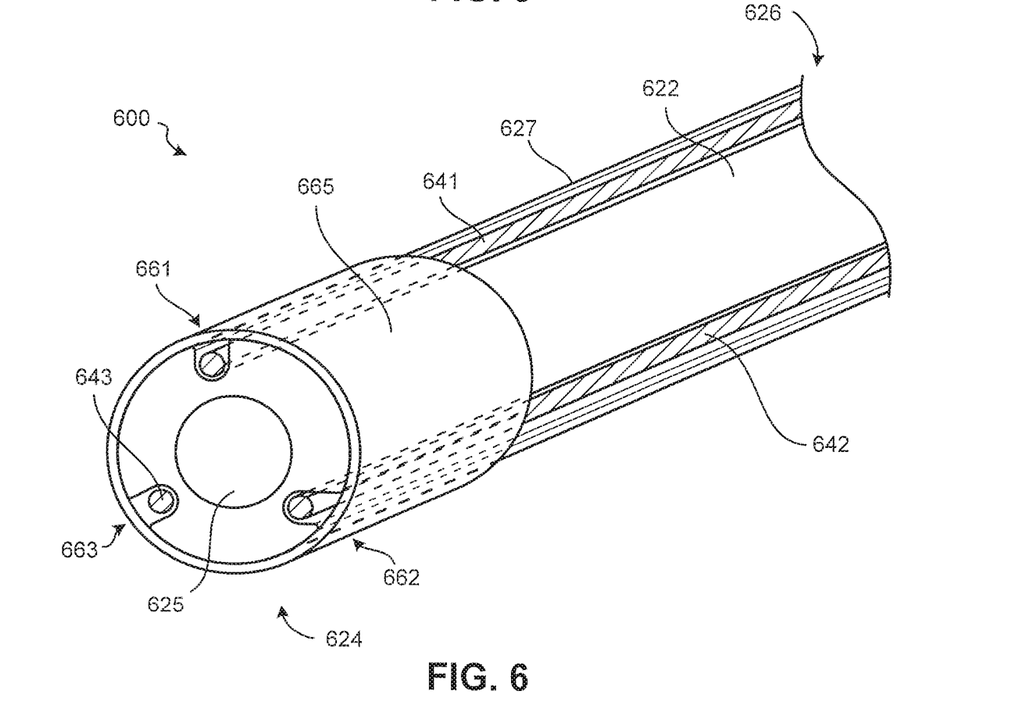
FIG. 6 is a perspective side view of an example catheter 600, according to some embodiments.

FIG. 6 illustrates a perspective side view of an example catheter 600 which may be utilized to detect drug extravasation, according to some embodiments. The catheter 600 may include a catheter lumen 622 having a proximal end 626, a distal end 624, an inner lumen surface 625, and an outer lumen surface 627. Although not shown in FIG. 6, in some embodiments, the distal end 624 of the catheter 600 may also be tapered, similar to the tapered distal end 24 of the catheter 22 illustrated in FIGS. 1A and 1B.

The catheter 600 may include a first electrode 641, a second electrode 642, and a third electrode 643. However, in other embodiments (not shown), the catheter 600 may only include two electrodes. In still other embodiments (not shown), the catheter 600 may include more than three electrodes.

In some embodiments, the first, second, and third electrodes 641, 642, 643 may include an electrically conductive material. In some embodiments, the electrically conductive material may include an electrically conductive metal. The first, second, and third electrodes 641, 642, 643 may also be spaced apart from each other along the catheter 600 and/or the outer lumen surface 627 at any distance.

In the embodiment shown in FIG. 6, the first, second, and third electrodes 641, 642, 643 may each be coupled to the catheter within a first channel 661, a second channel 662, and a third channel 663, respectively. The first, second, and third channels 661, 662, 663 may likewise extend along a length of the catheter 600. The first, second, and third channels 661, 662, 663 may include open channels formed within the body of the catheter lumen 622 that are open to the outer lumen surface 627 in order to allow electrical communication between the first, second, and third electrodes 641, 642, 643 via soft tissues that are between the first, second, and third electrodes 641, 642, 643.

The first, second, and third electrodes/channels 641, 642, 643, 661, 662, 663 may be also be formed via a co-extrusion process, or by any other suitable manufacturing process. In some embodiments, distal portions of the first, second, and third electrodes 641, 642, 643 may be electrically insulated from each other by a cover, a coating, a sleeve, or a cap. For example, in some embodiments, a cover 665 may be coupled to the distal end 624 of the catheter 600. The cover 665 may be configured to electrically isolate portions of the first, second, and third electrodes 641, 642, 643 from each other, which reside within a blood vessel. In this manner, the first, second, and third electrodes 641, 642, 643 at the distal portion of the catheter 600 (which may enter into a blood vessel) will not sense a drug within the blood vessel and produce a false positive indication of drug extravasation.

Figure 7:
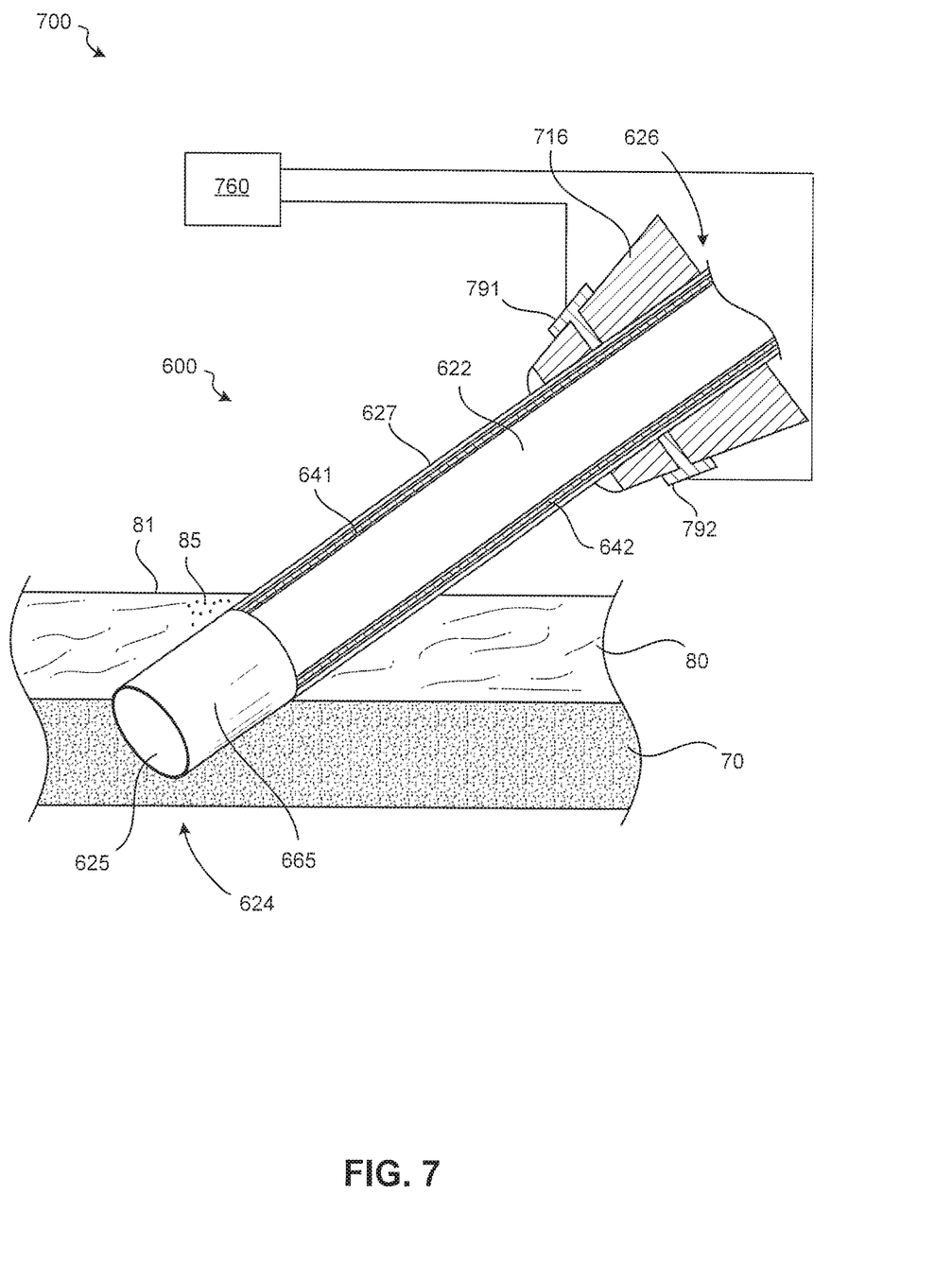
FIG. 7 is a partial cross-sectional side view of an example catheter system 700 which includes the catheter 600 of FIG. 6 inserted into tissue, according to some embodiments.

FIG. 7 is a partial cross-sectional side view of an example catheter system 700 including the catheter 600 of FIG. 6 inserted into tissue, according to some embodiments. The catheter system 700 may generally include the catheter 600, a catheter adapter 716, and a sensor 760. As shown in FIG. 7, the catheter 600 may be inserted through the skin 81 and into the soft tissue 80 until a distal portion of the catheter 600 enters the blood vessel 70.

The catheter system 700 may also include a first attachment feature 791 configured to couple the first electrode 641 to the sensor 760, and a second attachment feature 792 configured to couple the second electrode 642 to the sensor 760. The first and second attachment features 791, 792 may be coupled to, and/or integrated with, the catheter adapter 716. However, in other embodiments (not shown), the first and second attachment features 791, 792 may be directly coupled to, and/or integrated with, the catheter 600. In some embodiments, the first and second attachment features 791, 792 may traverse between an outer surface of the catheter adapter 716 and an inner surface of the catheter adapter 716. In some embodiments, the first attachment feature 791 may directly, or indirectly, contact the first electrode 641, and the second attachment feature 792 may directly, or indirectly, contact the second electrode 642. In some embodiments, the first and second attachment features 791, 792 may be configured to electrically couple the first and second electrodes 641, 642 to the sensor 760.

In some embodiments, the sensor 760 may be a drug sensor 760 configured to sense when a drug 85 has leaked out of the blood vessel 70 and into the soft tissue 80 adjacent the blood vessel 70 via an extravasation process. In this manner, the drug sensor 760 may detect when extravasation of the drug 85 has occurred and an indication of drug extravasation may be provided to the clinician via any suitable output device known in the art. As previously discussed, soft tissue containing an extravasated drug can exhibit different electrical, chemical, and/or physical characteristics in comparison to soft tissue that does not contain an extravasated drug. These differences in electrical, chemical, and/or physical characteristics may be utilized to indicate whether or not the soft tissue contains an extravasated drug in order to alert the clinician to a possible dangerous situation.

In some embodiments, the drug sensor 760 may be in communication with the first and second electrodes 641, 642 such that, when the distal end 624 of the catheter lumen 622 is successfully inserted into the blood vessel 70: (1) at least a portion of the first and second electrodes 641, 642 are embedded within the soft tissue 80 adjacent the blood vessel 70; (2) the first and second electrodes 641, 642 are in communication with each other through the soft tissue 80 between the first and second electrodes 641, 642; and (3) the drug sensor 760 detects whether extravasation of the drug 85 has occurred from the blood vessel 70 into the soft tissue 80 by sensing a characteristic associated with the soft tissue 80.

In some embodiments, the at least one characteristic associated with the soft tissue 80 containing the extravasated drug 85 includes at least one of: an impedance, a capacitance, a conductance, an inductance, an electromagnetic signal, a pressure, and a temperature. In some embodiments, the at least one characteristic may be measured directly, or indirectly. In some embodiments, determination of drug 85 extravasation may be based on a threshold value associated with the at least one characteristic, a change detected in the at least one characteristic as the soft tissue 80 becomes infused with the drug 85, and/or a relative difference that is detected in the at least one characteristic as the soft tissue 80 becomes infused with the drug 85.

Figure 8:
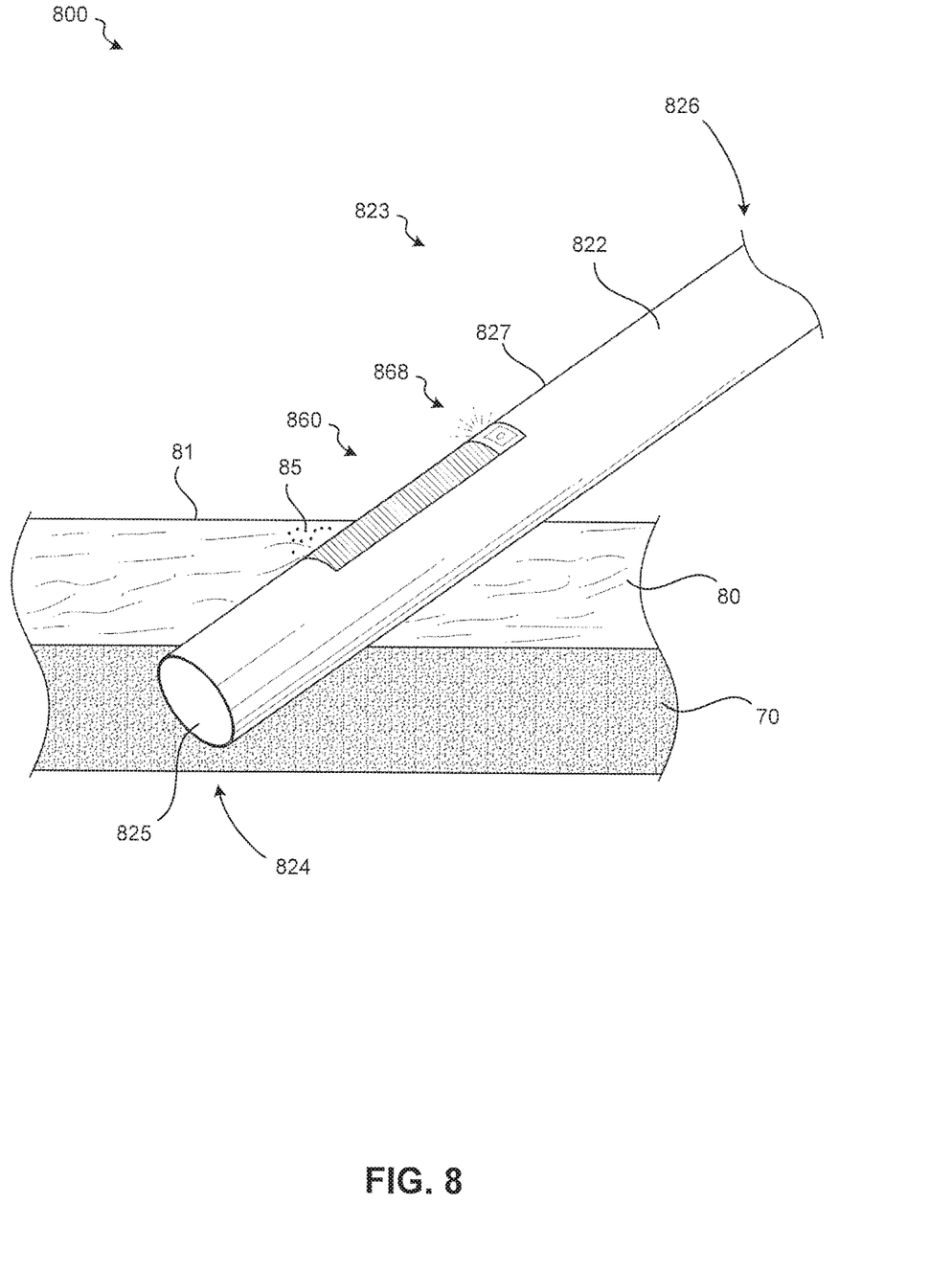
FIG. 8 shows an example catheter system 800 inserted into tissue, according to some embodiments.

FIG. 8 shows an example catheter system 800 inserted into tissue, according to some embodiments. The catheter system 800 may generally include a catheter 823 and a sensor 860. As shown in FIG. 8, the catheter 823 may be inserted through the skin 81 and into the soft tissue 80 until a distal portion of the catheter 823 enters the blood vessel 70.

The catheter 823 may include a catheter lumen 822 having a proximal end 826, a distal end 824, an inner lumen surface 825, and an outer lumen surface 827. Although not shown in FIG. 8, in some embodiments, the distal end 824 of the catheter 823 may also be tapered, similar to the tapered distal end 24 of the catheter 22 illustrated in FIGS. 1A and 1B.

In some embodiments, the sensor 860 may include a drug sensing chip 860 coupled to the outer lumen surface 827. The drug sensing chip 860 may include one or more sensors and/or one or more electrodes (not shown) arranged along its surface, which can be spaced apart from each other at one or more distances.

In some embodiments, at least a portion of the drug sensing chip 860 may be embedded within the soft tissue 80 adjacent to the blood vessel 70 when the distal end 824 of the catheter lumen 822 is inserted into the blood vessel 70. In this manner, the drug sensing chip 860 may detect when extravasation of a drug 85 has occurred from the blood vessel 70 and into the soft tissue 80 by sensing a characteristic associated with the soft tissue 80. If extravasation of a drug 85 has been detected, an indication of the drug extravasation event may be provided to the clinician via any suitable output device that is known in the art. In some embodiments, the output device may include an LED light 868 that may be configured to indicate the presence and/or absence of a drug 85 that has extravasated into the soft tissue 80.

As previously discussed, if the soft tissue 80 proximate the drug sensing chip 860 contains an extravasated drug 85, the soft tissue 80 can exhibit different electrical, chemical, and/or physical characteristics in comparison to soft tissue that is drug free. These differences in electrical, chemical, and/or physical characteristics may be utilized to determine whether or not the soft tissue 80 contains an extravasated drug 85 in order to alert the clinician to a possible dangerous situation.

In some embodiments, the at least one characteristic associated with the soft tissue 80 containing the extravasated drug 85 includes at least one of: an impedance, a capacitance, a conductance, an inductance, an electromagnetic signal (e.g., an infrared signal), a pressure, and a temperature. In some embodiments, the at least one characteristic may be measured directly, or indirectly. In some embodiments, determination of drug 85 extravasation may be based on a threshold value associated with the at least one characteristic, a change detected in the at least one characteristic as the soft tissue 80 becomes infused with the drug 85, and/or a relative difference that is detected in the at least one characteristic as the soft tissue 80 becomes infused with the drug 85.

It is to be understood that any of the embodiments of the present disclosure may be combined together in any number of different ways. As one non-limiting example, the embodiment of FIG. 2 may be combined with any one of (or any combination of) the embodiments of FIGS. 1A-1B and 3-8. As another non-limiting example, the embodiment of FIG. 3 may be combined with any one of (or any combination of) the embodiments of FIGS. 1A-2 and 4-8, and so forth.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

Standard medical directions, planes of reference, and descriptive terminology are employed in this specification. For example, anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. A sagittal plane divides a body into right and left portions. A midsagittal plane divides the body into bilaterally symmetric right and left halves. A coronal plane divides a body into anterior and posterior portions. A transverse plane divides a body into superior and inferior portions. These descriptive terms may be applied to an animate or inanimate body.

The phrases "connected to," "coupled to," "engaged with," and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in the Figures, the Figures are not necessarily drawn to scale unless specifically indicated.

While specific embodiments and applications of the present disclosure have been illustrated and described, it is to be understood that the scope of the appended claims is not limited to the precise configuration and components disclosed herein. Various modifications, changes, and variations which will be apparent to those skilled in the art may be made in the arrangement, operation, and details of the apparatus, systems, and methods disclosed herein.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

The invention claimed is:

1. A catheter system comprising:
a catheter, the catheter comprising:
    a catheter lumen comprising:
        a proximal end;
        a distal end;
        an inner lumen surface; and
        an outer lumen surface; and
    a first electrode coupled to the catheter lumen and spaced apart from the distal end of the catheter; and
    a second electrode coupled to the catheter lumen and spaced apart from the distal end of the catheter, wherein a distal end of the first electrode comprises a first portion that extends generally perpendicular to a proximal portion of the first electrode to form an L-shape, wherein a distal end of the second electrode comprises a second portion that extends generally perpendicular to a proximal portion of the second electrode to form another L-shape, wherein the first portion of the first electrode is spaced apart from and aligned with the second portion of the second electrode to create an electrode gap between the first portion of the first electrode and the second portion of the second electrode; and
a drug sensor in communication with the first and second electrodes coupled to the catheter lumen,
wherein when the distal end of the catheter lumen is inserted into a blood vessel of a patient:
    at least a portion of the first and second electrodes are embedded within a soft tissue of the patient adjacent the blood vessel,
    the first and second electrodes are in communication with each other through the soft tissue of the patient between the first and second electrodes, and
    the drug sensor detects whether extravasation of a drug has occurred from the blood vessel into the soft tissue of the patient by sensing a characteristic associated with the soft tissue of the patient, the characteristic comprising at least one of inductance, impedance, and capacitance.

2. The catheter system of claim 1, further comprising:
a catheter adapter coupled to the catheter, wherein the catheter adapter comprises an inner surface and an outer surface;
a first attachment feature configured to electrically couple the drug sensor to the first electrode; and
a second attachment feature configured to electrically couple the drug sensor to the second electrode, wherein the first attachment feature and the second attachment feature traverse between the inner surface of the catheter adapter and the outer surface of the catheter adapter.

3. The catheter system of claim 1, wherein:
the first electrode comprises an electrically conductive material deposited on the outer lumen surface; and
the second electrode comprises an electrically conductive material deposited on the outer lumen surface,
wherein the first and second electrodes are spaced apart from each other along the outer lumen surface.

4. The catheter system of claim 1, wherein the proximal portion of the first electrode proximal to the first portion is parallel to the proximal portion of the second electrode proximal to the second portion.

* * * * *